US010989517B2

(12) United States Patent
Zalevsky et al.

(10) Patent No.: US 10,989,517 B2
(45) Date of Patent: Apr. 27, 2021

(54) VIBRATION SENSING SYSTEM WITH WAVELENGTH ENCODING

(71) Applicant: CONTINUSE BIOMETRICS LTD., Tel Aviv (IL)

(72) Inventors: Zeev Zalevsky, Rosh HaAyin (IL); Javier Garcia, Valencia (ES)

(73) Assignee: CONTINUSE BIOMETRICS LTD., Tel Aviv (IL)

( * ) Notice: Subject to any disclaimer, the term of this patent is extended or adjusted under 35 U.S.C. 154(b) by 0 days.

(21) Appl. No.: 16/471,922

(22) PCT Filed: Nov. 21, 2017

(86) PCT No.: PCT/IL2017/051270
§ 371 (c)(1),
(2) Date: Jun. 20, 2019

(87) PCT Pub. No.: WO2018/116290
PCT Pub. Date: Jun. 28, 2018

(65) Prior Publication Data
US 2020/0103217 A1    Apr. 2, 2020

Related U.S. Application Data

(60) Provisional application No. 62/437,824, filed on Dec. 22, 2016.

(51) Int. Cl.
*G01B 11/02* (2006.01)
*G01B 9/02* (2006.01)
(52) U.S. Cl.
CPC .............. *G01B 9/02095* (2013.01)

(58) Field of Classification Search
CPC ............ G01B 9/02094; G01B 9/02095; G01B 9/02007; G01B 9/02019; G01B 11/162; G01B 2290/30; G01D 5/38
See application file for complete search history.

(56) References Cited

U.S. PATENT DOCUMENTS 8,638,991 B2    1/2014  Zalevsky et al.
9,668,672 B2    6/2017  Zalevsky et al.
(Continued)

FOREIGN PATENT DOCUMENTS

DE    19513233 C2    10/1996
EP    0 284 248 A1    9/1988
WO    03/046636 A1    6/2003

*Primary Examiner* — Tarifur R Chowdhury
*Assistant Examiner* — Jonathon Cook
(74) *Attorney, Agent, or Firm* — Browdy and Neimark, P.L.L.C.

(57) ABSTRACT

A system for use in inspection of a sample is described, the system comprises: an illumination unit configured to provide coherent illumination comprising a plurality of at least two wavelengths and direct said coherent illumination onto an inspection region of a sample; and a collection unit comprising at least one detector array and configured for collecting light returning from said inspection region and generate data indicative of speckle patterns in said plurality of at least two wavelengths at a predetermined sampling rate, wherein said illumination unit is configured for directing light components of said at least two wavelengths toward corresponding two or more segments of said inspection region, and wherein said data indicative of speckle patterns corresponding with said two or more segments.

18 Claims, 3 Drawing Sheets

(56) References Cited

U.S. PATENT DOCUMENTS

2012/0019809 A1* 1/2012 Shirley .............. G01B 11/2441
356/51
2012/0277755 A1 11/2012 Kohl-Bareis et al.
2015/0323311 A1* 11/2015 Muijs ................... A61B 5/0059
356/28.5

* cited by examiner

VIBRATION SENSING SYSTEM WITH WAVELENGTH ENCODING

TECHNOLOGICAL FIELD

The invention is in the field of vibration and motion sensing techniques and relates to a system for use in optical sensing of motion or vibrations of a target surface.

BACKGROUND

Optical monitoring of movement or vibrations of a sample provide a simple technique for providing information of biological tissue as well as other samples without a need of physical interactions other than illuminating of the sample.

Several techniques developed by the inventors of the present invention utilize illuminating of a region of a sample with coherent illumination and collecting light returning (reflected and scattered) from the sample for detecting variation in secondary speckle patterns formed by the returned light. The secondary speckle pattern is generally formed by interference of light components scattered from diffraction locations within the inspected region and is collected by imaging an intermediate plane along path of the returning light, e.g. utilizing defocused imaging unit.

U.S. Pat. No. 8,638,991 presents a method for imaging an object. The method comprises imaging a coherent speckle pattern propagating from an object, using an imaging system being focused on a plane displaced from the object.

U.S. Pat. No. 9,668,672 present a system and method for use in monitoring one or more conditions of a subject's body. The system includes a control unit which includes an input port for receiving image data, a memory utility, and a processor utility. The image data is indicative of data measured by a pixel detector array and is in the form of a sequence of speckle patterns generated by a portion of the subject's body in response to illumination thereof by coherent light according to a certain sampling time pattern. The memory utility stores one or more predetermined models, the model comprising data indicative of a relation between one or more measurable parameters and one or more conditions of the subject's body. The processor utility is configured and operable for processing the image data to determine one or more corresponding body conditions; and generating output data indicative of the corresponding body conditions.

General Description

As indicated above monitoring and detection of vibrations and/or movement of objects by identifying changes in secondary speckle patterns in light returning from the object provide an accurate and robust technique for non-invasive, non-contact sample inspection. In this connection, the sensibility of such detection technique is generally determined in accordance with imaging resolution of an imaging unit (camera) collecting image data indicative on the collected secondary speckle pattern relative to size distribution of speckles in the generated secondary speckle patterns.

Typically, the secondary speckle pattern formed by light returning (reflected and scattered) from the inspected region include speckles having certain size distribution. However, average size of the speckles can be generally estimated in accordance with area of the inspected region A, distance between the inspected region and the imaging unit L and wavelength λ of illumination used, providing general speckle with characteristic area of about $$S = (\lambda L / \sqrt{A})^2.$$

A characteristic dimension (length) of such speckles may thus be given by $$s = (\lambda L / \sqrt{A}).$$

This fact limits that area of the inspected region suitable for monitoring with a given system and given desired resolution, to provide image data in which speckles' size corresponding to a few pixels enabling resolving of the pixels.

The present invention provides a technique and a system for speckle-based monitoring of an object (e.g. biological tissue or other objects), utilizing wavelength encoding, enabling monitoring different segments of the inspection region and/or inspection region of increased area. In some additional configurations as described herein the present technique enables the use of wavelength encoding for monitoring sample with different depth penetration levels. To this end the technique of the invention utilizes illumination of an inspection region with coherent illumination of two or more wavelengths (wavelength ranges) and generally division of a desired inspection region to a plurality of segments. In some embodiments, the technique utilizes directing coherent illumination components of corresponding plurality of wavelengths onto the different segments using different wavelengths for monitoring corresponding segments. In some other configurations, the all wavelengths are directed at a common inspection region to provide monitoring of the region with different illumination characteristics, e.g. providing different penetration depths for the corresponding different wavelengths.

Light reflects/scattered from the different segments of the inspection region is collected by a collection unit such that the collected image data comprises data indicative of secondary speckle patterns formed by light components of each of the plurality of wavelengths used for illuminating the segments of the inspection region. The collected image data of each wavelength is indicative of light returning from the corresponding segment of the inspection region and can be used for monitoring parameters of the corresponding segment. Thus, the area of each of the different segments of the inspection region is generally selected, in combination with the corresponding wavelength, collection resolution (resolution of the imaging unit) and arrangement of the system, to provide desired monitoring resolution. Therefore, the use of plurality of wavelengths illuminating corresponding segments of the inspected region, enables efficient and accurate inspection of a region larger with respect to the region at can be inspected using single wavelength for given inspection resolution. More specifically, for given system parameters, such as geometric resolution of detection and distance from inspection region, the present technique is capable of monitoring a region that is N times larger with respect to region area monitored by the conventional speckle-based techniques, where N is the number of independent wavelength ranges used.

The technique of the invention, thus enables monitoring of a region having large area for given system configuration, while preserving speckle sizes and therefore monitoring sensitivity. Moreover, the technique enables separation between different portions of the inspected region and providing location specific data about selected parameters.

Thus, the present invention provides a system for use in inspection of parameters of a sample, the system comprising an illumination unit configured for providing coherent illuminating and directing said illumination onto a region of the sample to be inspected, and a collection unit configured for collecting light returning from said region of the sample and generating image data indicative of one or more secondary speckle patterns in the collected light. The illumination unit comprises a light source unit configured for providing coherent illumination of predetermined wavelength range comprising a selected plurality of wavelengths and may also comprise a spatial wavelength separation module configured for receiving light from the light source unit and separate light components of different wavelength towards corresponding different segments of the inspection region. Alternatively, the light source unit may comprise two or more light sources each configured to provide coherent illumination of selected wavelength, different than the other light sources, and direct the corresponding illumination components to a selected segment of the inspection region. The collection unit comprises at least one imager/camera unit, e.g. detector array and corresponding optical arrangement, configured for collecting light returning from the inspected region and generating image data indicative of secondary speckle patterns in two or more wavelengths provided by the illumination unit. More specifically, the collection unit is configured for simultaneously generating a plurality of image data pieces being defocused with respect to the inspection region, where each image data piece is indicative of one or more secondary speckle patterns associated with a corresponding wavelength of the plurality of wavelengths provided by the illumination unit. It should be noted that the different segments of the inspection region may be interfacing each other or including certain overlap between them. In some configurations, the different segments may be of selected distance between them, corresponding to separate points of the inspected region.

The collection unit may be configured for collecting a sequence of images at a desired sampling/frame rate, where each image comprising a plurality of image data pieces associated with the corresponding wavelengths. The sequence of images is transmitted for processing for determining variations in speckles patterns between consecutive image data pieces of the same wavelength, thereby generating data indicative of variation in orientation and/or movement within the corresponding segment of the inspection region. As indicated above, this enables high resolution monitoring of a larger inspection region with respect to previously described techniques, by effectively monitoring a plurality of segments of the inspection region in parallel to each other by wavelength multiplexing. Further, in some configurations, this technique enables simultaneous monitoring of a plurality of segments while simplifying collection of the monitoring data.

In some configurations, the spatial wavelength separation module of the illumination unit may be configured as one or more diffractive element, such diffractive elements may include dispersion grating element being reflecting or transmitting. The spatial wavelength separating module (SWS) is typically configured to varies direction of propagation of light components passing therethrough in accordance with wavelength of the light components. This provides light components of different wavelength propagating after interaction with the SWS along different directions respectively. The SWS may be configured for separating light components along one axis providing one dimensional arrangement of segments in the inception region, or for separating the light components along two axes providing two-dimensional arrangement of segments in the inspection region, being rectangular, hexagonal or any other two-dimensional arrangement. These configurations enable flexibility in selection of size and geometry of the inspection region in accordance with selected arrangement of the segments illuminated by the plurality of wavelengths.

As indicated above, the collection unit comprises one or more detector arrays (camera units) units and an optical arrangement. The optical arrangement is configured for imaging an intermediate plane onto the one or more detector arrays, such that the collected one or more images are defocused with respect to the inspection region, and provide image data of a secondary speckle pattern formed by the reflected/scattered light. More specifically, the optical arrangement may be configured for focusing with respect to a plane that the further or closer with respect to the inspection region and location of the one or more detector arrays. The collection unit may also include a spatial wavelength separating module (SWS) or one or more wavelength selective filters configures for assigning different detector arrays, or different regions of a detector array, for collection of light at the corresponding plurality of wavelengths to enable separation in collection of data associated with different wavelengths.

The technique of the invention may be used for monitoring parameters of an object, such as biological tissue (in vitro or in vivo), enabling detection of ongoing processes of the inspected tissue (e.g. detecting heart rate, muscle operation, glucose concentration, sound or acoustic data, elastic properties etc.). Additionally, or alternatively, the technique of the invention may be used for elastography measurements of a sample (being biological or not). For elastographic measurements, as well as other parameters, the technique may typically further comprise a stimulating unit configured for applying predetermined external stimulation on the sample.

Generally, according to some embodiments, the system may also comprise a control unit configured for receiving collected data associated with one or more sequences of images collected by the collection unit at a selected sampling rate, and for processing the collected data (e.g. the sequence of images) to determine one or more selected parameters of the inspection region. To this end the processing includes determining correlation between consecutive speckle patterns in collected image data pieces and determining one or more temporal correlation functions (e.g. at least one function for each wavelength of inspection) indicative of vibrations/movement in the corresponding segment of the inspection region, or as detected in the corresponding wavelength when different wavelengths illuminate common inspection region. The control unit may process image data pieces associated with different wavelengths separately, providing independent data about vibrations/movement in each segment (or penetration depth) of the inspection region in accordance with the corresponding wavelength.

Thus, according to one broad aspect, the present invention provides a system for use in inspection of a sample, the system comprising:

an illumination unit configured to provide coherent illumination comprising a plurality of at least two wavelengths and direct said coherent illumination onto an inspection region of a sample; and a collection unit comprising at least one detector array and configured for collecting light returning from said inspection region and generate data indicative of speckle patterns in said plurality of at least two wavelengths at a predetermined sampling rate, thereby providing plurality of at least two sequences of speckle patterns corresponding with said plurality of at least two wavelengths.

The illumination unit may be configured for directing light components of said at least two wavelengths toward a common inspection region, thereby enabling monitoring of said inspection region with plurality of at least two depths in accordance with penetration depth of the at least two wavelengths.

Alternatively, the illumination unit may be configured for directing light components of said at least two wavelengths toward corresponding two or more segments of said inspection region, and wherein said data indicative of speckle patterns corresponding with said two or more segments.

The illumination unit may comprise at least one light source unit configured for generating said coherent illumination of said plurality of wavelengths and a spatial wavelength separator module configured for receiving said coherent illumination and separating illumination components of different wavelength towards said two or more different segments of said inspection region.

The spatial wavelength separator module may be a diffractive element, refractive element or a combination of both.

According to some embodiments, the collection unit may comprise an optical arrangement, said optical arrangement and at least one detector array are located such that the optical arrangement forms on the at least one detector array an image corresponding to an intermediate plane of light propagation between the inspection region and the collection region.

Alternatively, in some embodiments, the collection unit may comprise an optical arrangement and at least one detector array, arranged between them for collection of defocused image data of said inspection region.

Generally, the collection unit may further comprise a wavelength separating module configured for separating light components of different wavelength to thereby enable said at least one detector array to distinguish between light components of said plurality of at least two wavelengths. The wavelength separating module may be diffractive element, refractive element. Further, the wavelength separating module may comprise one or more wavelength selective filters.

According to some embodiments, the collection unit may be configured for generating one or more sequences of image data in a selected sampling rate, said image data comprises a plurality of image data pieces associated with said plurality of at least two wavelengths.

The correlation between consecutive image data pieces may be associated with a common wavelength being indicative of variation in orientation or movement within a corresponding segment of the inspection region being illumination by said common wavelength.

In some embodiments, the illumination unit may be configured to provide illumination with a plurality of N wavelengths, said collection unit is configured to provide effective monitoring of a region of area S, such that system is configured for monitoring of an inspection region of area SN.

According to another broad aspect, the present invention provides a method for use in monitoring a sample, the method comprising: directing coherent illumination comprising two or more wavelength ranges onto an inspection region on the sample, and collecting light components returning from said region of interest and generating a plurality of image data pieces indicative of secondary speckle patterns in said light components; said plurality of image data pieces comprising two or more sequences of image data pieces associated with speckle patterns in said two or more wavelength ranges respectively.

In some embodiments, said directing coherent illumination comprising two or more wavelength ranges may comprise directing light components of each wavelength range to illuminate a corresponding segment of said inspection region, thereby illuminating two or more segments of the inspection region using corresponding two or more wavelengths. Additionally, said directing coherent illumination may comprise directing said coherent illumination onto a spatial wavelength separator for splitting said two or more wavelength ranges toward said corresponding segments of the inspection region. The two or more segments may be partially parallel, interfacing or spaced apart.

In some other embodiments, said directing coherent illumination comprising two or more wavelength ranges may comprise directing light components of the two or more wavelengths onto a common inspection region, said two or more sequences of image data pieces thereby indicative of monitoring of said inspection region with different penetration depths.

Generally, according to some embodiments, said collecting light components returning from said region of interest comprises using an optical arrangement and one or more detector arrays arranged to provide defocused image data with respect to said inspection region.

According to yet another broad aspect of the invention there is provided a system for use in inspection of a sample, the system comprising: an illumination unit configured to provide coherent illumination comprising a plurality of at least two wavelengths and direct said coherent illumination onto an inspection region of a sample; and a collection unit comprising at least one detector array and configured for collecting light returning from said inspection region and generate data indicative of speckle patterns in said plurality of at least two wavelengths at a predetermined sampling rate.

According to some embodiments, said illumination unit may comprise at least one light source unit configured for generating said coherent illumination of said plurality of wavelengths and a spatial wavelength separator module configured for receiving said coherent illumination and separating illumination components of different wavelength towards corresponding different segments of said inspection region.

The spatial wavelength separator module may be a diffractive element.

According to some embodiments, said collection unit may comprise an optical arrangement, said optical arrangement and at least one detector array are located such that the optical arrangement forms on the at least one detector array an image corresponding to an intermediate plane of light propagation between the inspection region and the collection region.

According to some embodiments, the collection unit may further comprise a wavelength separating module configured for separating light components of different wavelength to thereby enable said at least one detector array to distinguish between light components of said plurality of at least two wavelengths.

The wavelength separating module may be a diffractive element or comprises one or more wavelength selective filters.

According to yet some embodiments, said collection unit may be configured for generating a sequence of image data in a selected sampling rate, said image data comprises a plurality of image data pieces associated with said plurality of at least two wavelengths.

Generally according to some embodiments, correlation between consecutive image data pieces associated with a common wavelength being indicative of variation in orientation or movement within a segment of the inspection region being illumination by said common wavelength.

According to an additional broad aspect of the invention, there is provided a system for use in inspection of a sample, the system comprising:
- an illumination unit configured to provide coherent illumination comprising a plurality of at least two wavelengths and direct said coherent illumination onto an inspection region of a sample; and
- a collection unit comprising at least one detector array and configured for collecting light returning from said inspection region and generate data indicative of speckle patterns in said plurality of at least two wavelengths at a predetermined sampling rate.

According to some embodiments, said illumination unit comprises at least one light source unit configured for generating said coherent illumination of said plurality of wavelengths and a spatial wavelength separator module configured for receiving said coherent illumination and separating illumination components of different wavelength towards corresponding different segments of said inspection region. Said spatial wavelength separator module may be a diffractive element.

Additionally, or alternatively, said collection unit may comprise an optical arrangement, said optical arrangement and at least one detector array are located such that the optical arrangement forms on the at least one detector array an image corresponding to an intermediate plane of light propagation between the inspection region and the collection region.

The collection unit may further comprise a wavelength separating module configured for separating light components of different wavelengths to thereby enable said at least one detector array to distinguish between light components of said plurality of at least two wavelengths. Said wavelength separating module may be a diffractive element or comprises one or more wavelength selective filters.

According to some embodiments, the collection unit may be configured for generating a sequence of image data in a selected sampling rate, said image data comprises a plurality of image data pieces associated with said plurality of at least two wavelengths. A correlation between consecutive image data pieces associated with a common wavelength may be indicative of variation in orientation or movement within a segment of the inspection region being illumination by said common wavelength.

According to some embodiments, said illumination unit is configured to provide illumination with a plurality of N wavelengths, said collection unit is configured to provide effective monitoring of a region of area S, such that system is configured for monitoring of an inspection region of area SN. Thus, the technique of the present invention may provide effective monitoring of an inspection region N times larger with respect to inspection region monitored by a speckle-based system with given collection configuration. Such collection configuration parameters typically include geometric resolution of the detector array and distance from the inspection region.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
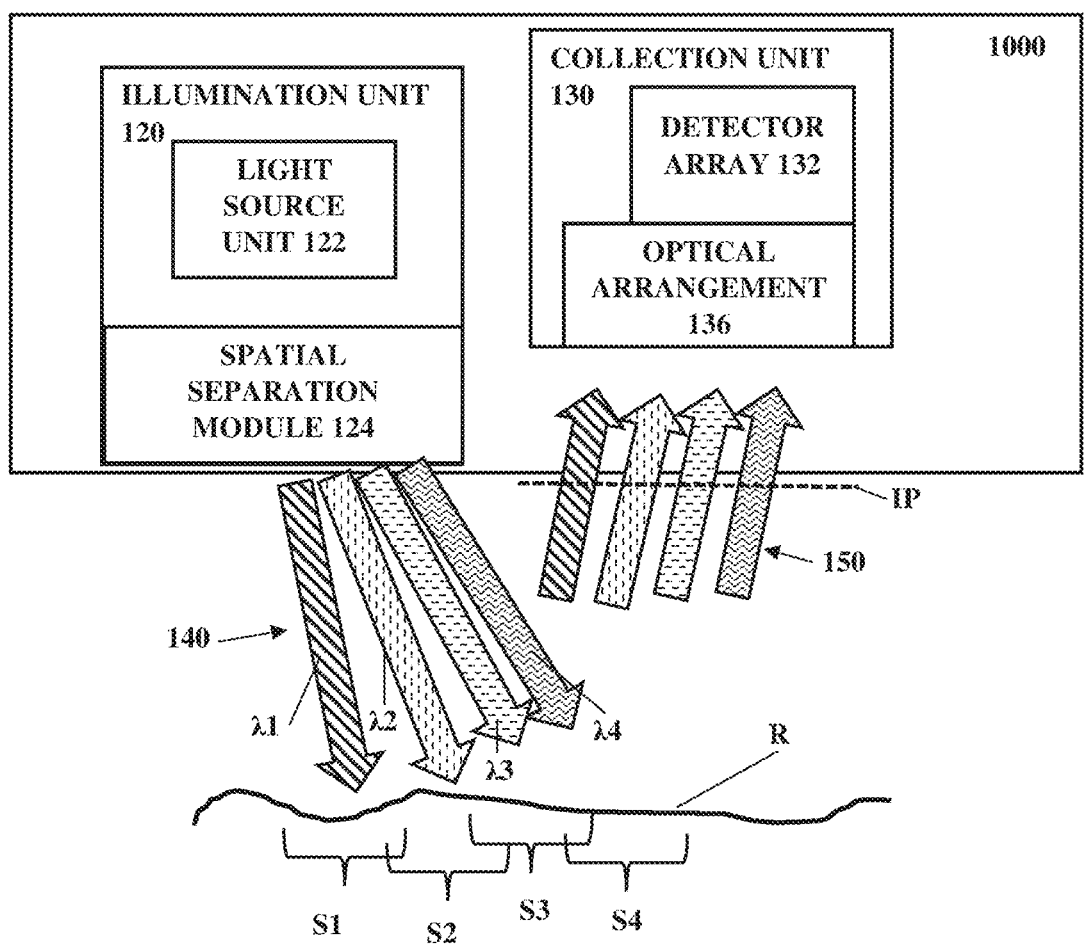
FIG. 1 illustrates schematically a sample inspection system according to the present invention.

Reference is made to FIG. 1 illustrating schematically a system 1000 for use in monitoring and inspection of a sample according to the present invention. The system 1000 is configured for optically monitoring inspection region R. More specifically, the system may be configured for monitoring segments S1-S4 of the inspection region R, enabling separate monitoring of the different segments using corresponding different wavelengths. In some configuration, the system may be configured for monitoring inspection region R while enabling separate inspection of different characteristics of penetration depths of the inspection region. To this end the system 1000 is configured for providing coherent illumination 140 including a plurality of wavelengths (having plurality of two or more wavelength ranges, e.g. $\lambda1$-$\lambda4$) and directing it onto an inspection region R of a sample, and for collecting light returning 150 by reflection and scattering from the inspection region R by a collection unit. The system 1000 may utilize data indicative of variation in time of one or more secondary speckle patterns in the collected light 150 for determining parameters of the sample. Such parameters may include data about movement, vibrations, response to external stimulation and other parameters of the sample, and accordingly one or more characteristics of the sample or operation thereof manifested in vibrations/movement of the inspection region.

The system 1000 includes an illumination unit 120 configured for providing coherent illumination 140 of two or more wavelengths and directing it onto inspection region R of the sample, and a collection unit 130 configured for collecting light returning 150 from the sample and generating image data pieces indicative of secondary speckle patterns in the collected illumination. The illumination unit 120 includes one or more light sources, e.g. light source unit 122 configured to provide coherent illumination having a plurality of wavelength ranges (e.g. broadband laser) for providing the two or more wavelengths. Additionally, the illumination unit 120 may also include a spatial wavelength separating module (SWS) 124 configured for varying direction of propagation of different wavelengths provided by the light source unit 122. The SWS module 124 may for example be a diffractive element such as a dispersion grating element, or a refractive element such as prism, configured for directing light components of different wavelength to propagate at different angles. The illumination unit may also include one or more optical elements such as lenses, prisms and/or mirrors configured for directing illumination onto the selected segments of inspection region R of the sample. The SWS module 124 thus varies direction of propagation of output light components in accordance with wavelengths thereof and is configured for directing different light components, e.g. light components of wavelength $\lambda1$-$\lambda4$ towards corresponding segments S1-S4 of the inspection region R.

In this connection, it should be noted that, for simplicity, the present technique is herein described as utilizing spatial wavelength separating module 124 in the illumination unit 120 for illuminating different segments of the inspection region R with corresponding different wavelengths. It should however be understood that the present technique may also utilize illumination unit configured for directing coherent illumination of two or more wavelengths directed at a common inspection region R. This configuration enables the use of selected wavelength for inspection/monitoring of the inspection region with different penetration depths of light, thereby enabling collection of data about sample properties with certain depth resolved information. Additionally, selected wavelengths may be associated with different characteristics of the sample enabling combined monitoring of several sample characteristics using different wavelengths. In such configurations, the collection unit 130 may still be configured for detection of different wavelength and generating corresponding image data pieces for separate monitoring of the sample with the two or more wavelengths used for illumination.

Thus, the illumination unit 120 is configured for dividing the inspection region to a plurality of segments, 4 segments in this non-limiting example, by providing separated illumination components to the different segments. Each segment is illuminated with light of different wavelength that can be collected and processed separately. The different segments may be arranged along an axis providing a one-dimensional arrangement or along two axes providing a two-dimensional arrangement, e.g. rectangular, hexagonal or any other two-dimensional configuration. One dimensional arrangement of the wavelengths' segments may be provided by a one-dimensional diffractive granting of the SWS 124. To provide two-dimensional arrangement of the wavelengths' segments, the SWS 124 may utilize two one-dimensional diffractive gratings arranged one after the other where the two diffractive gratings are aligned perpendicular to each other.

Additionally, segments dividing the inspection region may be overlapping, interfacing each other or spaced apart between them. More specifically, the illumination unit 120 illuminating the inspection region R by a plurality of illumination spots associated with different wavelengths in accordance with the bandwidth of the light source unit 122, or number of different light sources therein, and the dispersion arrangement of the SWS 124, such that each illumination spot defines a segment of the inspection region. As indicated above, the spots of different wavelengths may be overlapping at the boundaries between them thereby illuminating certain points of the inspection region R with two or more wavelengths, interfacing vie thin boundaries where the illumination intensity is reduced, or spaced apart between them, as the case may be.

As light from the illumination unit 120 impinges onto the different segments of the inspection region R, light components are reflected and scattered, forming light channel 150 returning from the surface of the sample. The collection unit 130 is configured for collecting light returned 150 from the inspection region R and generating image data pieces indicative of secondary speckle pattern formed in the collected light due to self-interference of light components upon scattering from the inspection region R. To this end the collection unit includes one or more detector arrays 132 and at least one optical arrangement 136. The optical arrangement 136 is configured to provide defocused imaging of the inspection region R into the one or more detector arrays 132. More specifically, the optical arrangement is configured for imaging onto the one or more detector array 132, an object plane corresponding to an intermediate plane IP located away from the inspection region R, e.g. between the inspection region R and the optical arrangement, or further from the inspection region R. The detector array 132 is configured for collecting the image data associated with secondary speckle patterns and generate corresponding image data pieces at a desired sampling rate and geometrical resolution to thereby generate image data sequence. The image data sequence may be transmitted for processing, e.g. by a local or remote control unit or processing utility, being integral to the system or separated therefrom the processing is configured for determining data about movement, variation in location and/or orientation of regions within the inspection region R and for determining one or more corresponding selected parameters of the sample.

As indicated above, different segments of the inspection region R, e.g. segments S1-S4, are illuminated with optical radiation of selected different wavelengths ranges (e.g. $\lambda 1$-$\lambda 4$). The collection unit 130 is configured to generate, in response to collection of light returning from the sample, image data including a plurality of image data pieces associated with the different wavelengths $\lambda 1$-$\lambda 4$ used. The different image data pieces associated with corresponding wavelengths provide data indicative of the different segments of the inspection region.

The collection unit 130 may include a wavelength separator module such as dispersion grating, a set of wavelength selective filters or any other type of wavelength separator configured to enable the detector array 132 to distinguish between the different wavelengths and provides corresponding plurality of image data pieces. In some configuration, using specific wavelength, the collection unit 130 may include a detector array 132 including Bayer filter, enabling separation of RGB related wavelengths.

Figure 2:
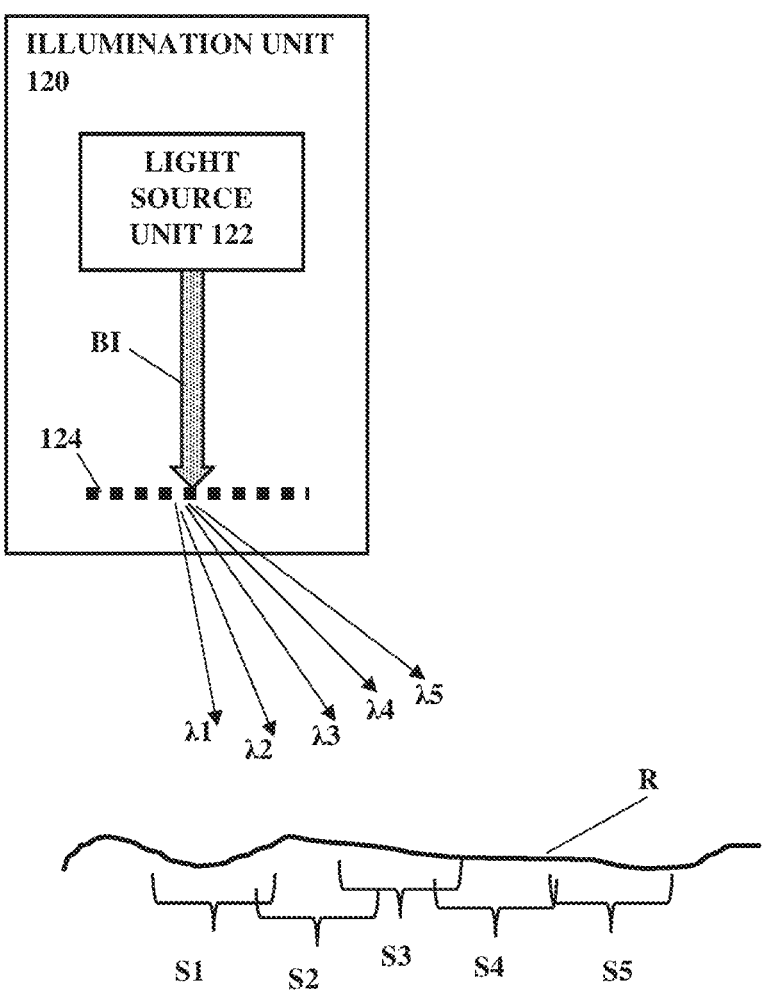
FIG. 2 exemplifies structure and operation scheme of an illumination unit according to some embodiments of the invention.

Reference is made to FIG. 2 illustrating an illumination unit 120 according to some embodiments of the invention. The illumination unit 120 as shown herein includes a light source unit 122 and a diffractive element 124 configured for spatially separating light components of different wavelength. For example, the diffractive elements may be configured as a dispersion grating. The illumination unit 120 may also include one or more optical elements 126 (shown in dashed line) configured for directing and manipulating the generated and emitted illumination towards the desired region R of the sample. The light source unit 122 is configured to provide broad band coherent illumination BI including selected number of wavelength, e.g. having certain selected bandwidth and coherence length. Generally, the light source unit 122 may be a broad band laser unit or an arrangement of laser units emitting light is selected wavelength ranges providing the desired plurality of wavelengths.

The light BI provided by the light source unit is directed towards a spatial wavelength separating module 124, which in this example is provided by a dispersion grating, configured for directing light components of different wavelengths towards corresponding different spatial directions. The SWS module 124 is configured, in combination with corresponding one or more optical elements 126 or not, to direct light components of different wavelength (e.g. $\lambda 1$-$\lambda 5$) to illuminate corresponding segments (e.g. S1-S5) of the sample. Typically, the number of different regions may be selected in accordance with number of distinct wavelengths, or bandwidth of wavelength range, reducing possible overlap in detection of the wavelengths. Further. As indicated above, the segments, S1-S5 in this example, may be spaced apart between them, interfacing or partially overlapping In some configurations, the SWS 124 may be configured to reduce intensity of light components propagating at the zero order of diffraction to thereby direct high intensity of light propagating in desired directions to impinge onto the corresponding segments of the inspection region R. This is to enable spatial separation between wavelengths, as the zero order is typically similar for different wavelengths, while higher diffraction orders are associated with angular variations between wavelengths. As indicated above, in some configurations, the illumination unit 120 may also utilize one or more optical elements 126 configured for directing light components of the different wavelengths $\lambda 1$-$\lambda 5$ onto the corresponding segments with desired level of overlapping between segments.

Figure 3:
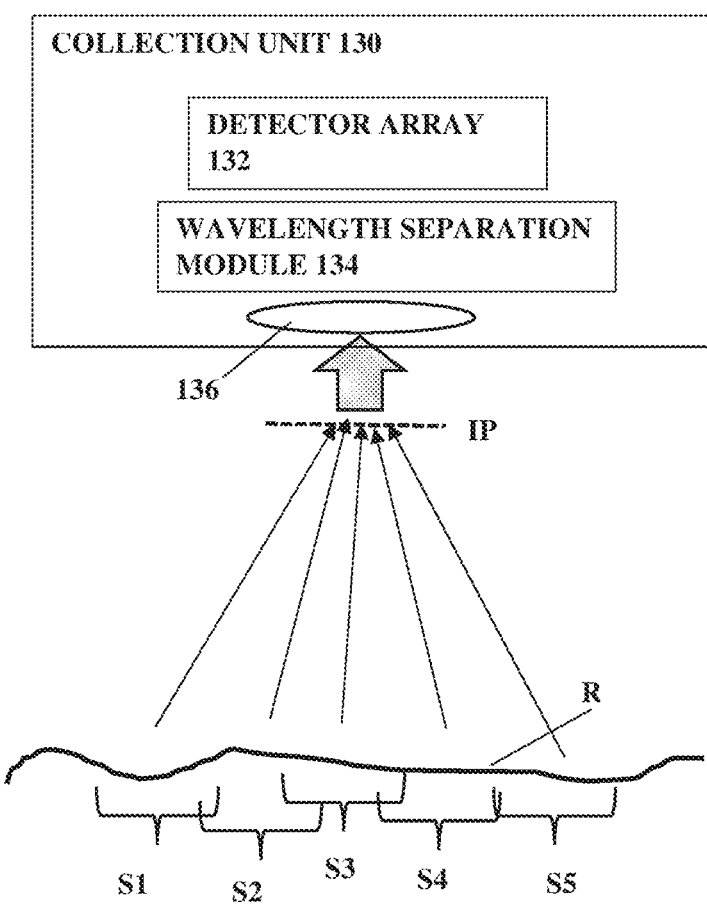
FIG. 3 exemplifies structure and operation scheme of a collection unit according to some embodiments of the invention.

The collection unit 130, according to some embodiments of the invention, is illustrated in FIG. 3. As shown, the collection unit 130 includes an optical arrangement 136 and one or more detector arrays 132, where the optical arrangement 136 and the detector array(s) 132 are configured such that the image formed on the detector array 132 is defocused with respect to the inspection region R. More specifically, the configuration of collection unit 130 corresponds to imaging of an intermediate plane along light propagation into the collection unit, or further from the inspection region R. Thus, the collection unit 130 is configured to operate as a camera unit, being defocused with respect to the inspection region R. This configuration of the optical arrangement 136 and the one or more detector arrays 132 provides for forming image data corresponding to one or more secondary speckle patterns associated with light scattering/reflecting from the inspection region R. The collection unit may typically also include a wavelength separation module 134 configured for separating light components of different wavelengths, selected based on the wavelengths provided by the illumination unit 120. The light separation unit 134 is configured to enable the one or more detector arrays 132 to distinguish between collection light components of the different wavelengths (e.g. $\lambda 1$-$\lambda 5$) and thus generate corresponding plurality of image data pieces, each associated with different wavelength. For example, the light separation unit 134 may include two or more wavelength selective filters, diffractive element or prism allowing different wavelengths to be collected by different portions of the detector array 132 or by different detector arrays. In some configurations, the light separation unit may be manifested by Bayer filter providing RGB separation to a polychromatic detector array.

Generally, according to the present invention, the collection unit 130 is configured for collecting light of a plurality of wavelength, and at each frame of light collection, form a plurality of image data pieces corresponding to the different wavelengths (e.g. $\lambda 1$-$\lambda 5$). The wavelength separating module 134 of the collection unit 134 may be configured as a spatial wavelength separating module such as one or more diffractive elements (e.g. dispersion grating), or refractive elements (e.g. prism) configured to direct light components of different wavelengths toward corresponding different detector arrays 132 or to corresponding regions of a common detector array 132. Additionally, or alternatively, the wavelength separating module 134 may be configured of a plurality of wavelength selective filters configured with a plurality of transmitting regions, each transmitting light of one selected wavelength of the plurality of wavelength provided by the illumination unit 120.

It should be noted, and is indicated above, that as the collection unit is configured for collecting defocused image data, e.g. associated with an intermediate plane along light propagation thereto, there need not be correlation between spatial location of the regions of the detector array 132 configured (by the wavelength separating module 134) for collecting light of different wavelengths, and the segments S1-S5 associated with these wavelengths. Thus, the collection unit may generally be oriented in general direction of the inspection region R, to allow efficient collection of light, while the wavelength separating module 134 is configured for separating collected light for generating plurality of image data pieces associated with the different wavelengths.

Generally, the illumination unit 120 may be operated continuously to illuminate the inspection region R while the collection unit 130 may operate at a selected sampling rate to provide one or more sequences of image data pieces. More specifically, the collection unit generates a plurality of sequences of image data pieces respectively associated with the plurality of wavelengths provided by the illuminating unit. This allows efficient and simultaneous monitoring of a region R of a sample having area larger than that can be monitored using a single wavelength for given monitoring resolution. More specifically, average size of speckle in speckle patterns formed in light returning from the sample is dependent by the wavelength and the distance of the collection unit 130 (or the intermediate plane IP) from the inspection region R of the sample and is inversely dependent on the area of the illuminated region of the inspection region R. Thus, in the conventional techniques, to increase resolution using given geometrical resolution of the detector array and arrangement of the collection unit 130, the inspection region R may be smaller. The technique of the present invention utilizes plurality of inspection segments of the inspection region, and may benefit from greater geometrical resolution of the detector array 132 (e.g. to provide desired resolution of speckle pattern detection for each of the wavelengths used).

Accordingly, the present technique utilizes optical inspection of a selected region using a plurality of wavelength directed at an inspection region of a sample and collected to generate corresponding set of image data pieces indicative of properties of the sample. The plurality of wavelengths may be directed at a common inspection region or a corresponding plurality of segments thereof, while collected for enabling separated monitoring of the inspection region with different wavelength. The present technique utilizes speckle-based inspection technique enabling high accuracy and non-contact monitoring of various properties as described above.

The invention claimed is:

1. A system for use in inspection of a sample, the system comprising:
   an illumination unit configured to provide coherent illumination comprising a plurality of at least two wavelengths and direct said coherent illumination onto an inspection region of a sample; and
   a collection unit comprising at least one detector array and configured for collecting light returning from said inspection region and generate data indicative of speckle patterns in said plurality of at least two wavelengths at a predetermined sampling rate and generating a plurality of sequences of speckle patterns corresponding with said plurality of at least two wavelengths such that each sequence is formed by image data indicative of speckle patterns associated with a common wavelength range;
   wherein said illumination unit is configured for directing light components of said at least two wavelengths toward corresponding two or more segments of said inspection region, and wherein said data indicative of speckle patterns corresponding with said two or more segments.

2. The system of claim 1, wherein said illumination unit is configured for directing light components of said at least two wavelengths toward a common inspection region, thereby enabling monitoring of said inspection region with plurality of at least two depths in accordance with penetration depth of the at least two wavelengths.

3. The system of claim 1, wherein said illumination unit comprises at least one light source unit configured for generating said coherent illumination of said plurality of wavelengths and a spatial wavelength separator module configured for receiving said coherent illumination and separating illumination components of different wavelength towards said two or more different segments of said inspection region.

4. The system of claim 3, wherein said spatial wavelength separator module is a diffractive element.

5. The system of claim 1, wherein said collection unit comprises an optical arrangement, said optical arrangement and at least one detector array are located such that the optical arrangement forms on the at least one detector array an image corresponding to an intermediate plane of light propagation between the inspection region and the collection region.

6. The system of claim 1, wherein said collection unit comprises an optical arrangement and at least one detector array, arranged between them for collection of defocused image data of said inspection region.

7. The system of claim 5, wherein the collection unit further comprises a wavelength separating module configured for separating light components of different wavelength to thereby enable said at least one detector array to distinguish between light components of said plurality of at least two wavelengths.

8. The system of claim 7, wherein said wavelength separating module is a diffractive element or comprises one or more wavelength selective filters.

9. The system of claim 1, wherein said collection unit is configured for generating one or more sequences of image data in a selected sampling rate, said image data comprises a plurality of image data pieces associated with said plurality of at least two wavelengths.

10. The system of claim 9, wherein correlation between consecutive image data pieces associated with a common wavelength being indicative of variation in orientation or movement within a corresponding segment of the inspection region being illumination by said common wavelength.

11. The system of claim 1, wherein said illumination unit is configured to provide illumination with a plurality of N wavelengths, said collection unit is configured to provide effective monitoring of a region of area S with selected desired resolution, such that system is configured for monitoring of an inspection region of area S times the number N, thereby enlarging inspection region for given collection unit.

12. A method for use in monitoring a sample, the method comprising: directing coherent illumination comprising two or more wavelength ranges onto an inspection region on the sample, and collecting light components returning from said region of interest and generating a plurality of image data pieces indicative of secondary speckle patterns in said light components, said plurality of image data pieces comprising two or more sequences of image data pieces associated with speckle patterns in said two or more wavelength ranges respectively, and processing said two or more sequences of image data pieces by determining correlations between speckle patterns of common wavelength range; wherein said directing coherent illumination comprising two or more wavelength ranges comprises directing light components of each wavelength range to illuminate a corresponding segment of said inspection region, thereby illuminating two or more segments of the inspection region using corresponding two or more wavelengths and generating independent data on vibrations or movement in said two or more segments of the inspection region in accordance with the corresponding wavelength.

13. The method of claim 12, wherein said directing coherent illumination comprises directing said coherent illumination onto a spatial wavelength separator for splitting said two or more wavelength ranges toward said corresponding segments of the inspection region.

14. The method of claim 12, wherein said two or more segments being partially parallel.

15. The method of claim 12 wherein said two or more segments are interfacing.

16. The method of claim 12, wherein said two or more segments are spaced apart.

17. The method of claim 12, wherein said directing coherent illumination comprising two or more wavelength ranges comprises directing light components of the two or more wavelengths having respectively two or more penetration depth into the sample onto a common inspection region, said two or more sequences of image data pieces being indicative of light components returning from said inspection region with different penetration depths.

18. The method of claim 12, wherein said collecting light components returning from said region of interest comprises using an optical arrangement and one or more detector arrays arranged to provide defocused image data with respect to said inspection region.

* * * * *